United States Patent
Zhang et al.

(10) Patent No.: US 7,205,452 B2
(45) Date of Patent: Apr. 17, 2007

(54) CONTROL OF BACTERIAL INFECTION BY QUENCHING QUORUM-SENSING OF PLANT PATHOGENIC BACTERIA

(75) Inventors: Lianhui Zhang, Singapore (SG); Yihu Dong, Singapore (SG); Jinling Xu, Singapore (SG); Xifen Zhang, Singapore (SG)

(73) Assignee: Agency for Science, Technology and Research, Centros (SG)

( * ) Notice: Subject to any disclaimer, the term of this patent is extended or adjusted under 35 U.S.C. 154(b) by 42 days.

(21) Appl. No.: 10/470,294

(22) PCT Filed: Jan. 29, 2001

(86) PCT No.: PCT/SG01/00012

§ 371 (c)(1),
(2), (4) Date: Jan. 20, 2004

(87) PCT Pub. No.: WO02/061099

PCT Pub. Date: Aug. 8, 2002

(65) Prior Publication Data

US 2004/0139495 A1 Jul. 15, 2004

(51) Int. Cl.
*C12N 15/31* (2006.01)
*C12N 15/82* (2006.01)
*A01H 5/00* (2006.01)

(52) U.S. Cl. .................. 800/279; 800/278; 800/298; 435/468

(58) Field of Classification Search ............... 800/288, 800/278, 279, 298; 435/468
See application file for complete search history.

(56) References Cited

FOREIGN PATENT DOCUMENTS

| WO | WO 00/09696 | * | 2/2000 |
| WO | WO 01 02578 | | 1/2001 |
| WO | WO 01/02578 A1 | | 1/2001 |

OTHER PUBLICATIONS

Dong Yi-Hu et al., "AiiA, an enzyme that inactivates the acylhomoserine lactone quorum-sensing signal and attenuates the virulence of *Erwinia carotovora*" Proceedings of the National Academy of Sciences of USA, National Academy of Science, Washington, US, vol. 97, No. 7, Mar. 28, 2000, pp. 3526-3531, XP002166712.

De La Cruz, "Quorum Quenching by *Bacillus cereus* UW85," Univ. Of Wisconsin, Aug. 10, 2001, 13 pgs.

Dong et al., "Identification of quorum-quenching N-Acyl homoserine lactonases from *Bacillus* species," Appl. Environ. Microbiol. 68(4);1754-1759, 2002.

Dong et al., GenBank accession No. AF350927, from Appl. Environ. Microbiol. 68(4):1754-1759, 2002.

Dong et al., GenBank accession No. AF350928, from Appl. Environ. Microbiol. 68(4):1754-1759, 2002.

Dong et al., GenBank accession No. AF350929, from Appl. Environ. Microbiol. 68(4):1754-1759, 2002.

Dong et al., GenBank accession No. AF350930, from Appl. Environ. Microbiol. 68(4):1754-1759, 2002.

Dong et al., GenBank accession No. AF350931, from Appl. Environ. Microbiol. 68(4):1754-1759, 2002.

Dong et al., GenBank accession No. AF350932, from Appl. Environ. Microbiol. 68(4):1754-1759, 2002.

Dong et al., GenBank accession No. AF350933, from Appl. Environ. Microbiol. 68(4):1754-1759, 2002.

Dong et al., GenBank accession No. AF350934, from Appl. Environ. Microbiol. 68(4):1754-1759, 2002.

Dong et al., GenBank accession No. AF350935, from Appl. Environ. Microbiol. 68(4):1754-1759, 2002.

Dong et al., "AiiA, an enzyme that inactivates the acylhomoserine lactone quorum-sensing signal and attenuates the virulence of *Erwinia carotovora*," Proc. Natl. Acad. Sci., 97(7):3526-31, 2000.

Dunphy et al., "A homoserine lactone autoinducer regulates virulence of an insect-pathogenic bacterium," *Xenorhabdus nematophilus* (*Enterobacteriaceae*), J. Bacteriol., 179(17):5288-5291, 1997.

Flavier et al., "Identification of 3-hydroxypalmitic acid methyl ester as a novel autoregulator controlling virulence in *Ralstonia solanacearum*." Mol. Microbiol., 26(2): 251-259, 1997.

Lee et al., "Genes encoding the N-Acyl homoserine lactone-degrading enzyme are widespread in many subspecies of *Bacillus thuringiensis*," Appl. Env. Microbiol., 68(8):3919-3924, 2002.

Pearson et al., "Structure of the autoinducer required for expression of *Pseudomonas aeruginosa* virulence genes," Proc. Natl. Acad. Sci. USA, 91:197-201, 1994.

Robson et al., "Bacterial N-acyl-homoserine-lactone-dependent signaling and its potential biotechnological applications," Trends Biotechnol., 15:458-464, 1997.

Tait et al., "Disruption of quorom sensing in seawater abolishes attraction of zoospores of the green alga *Ulva* to bacterial biofilms," Envir. Microbiol., 7(2):229, 2005. (Abstract).

Ulrich, "Quorum quenching: enzymatic disruption of N-acylhomoserine lactone-mediated bacterial communication in *Burkholderia thailandensis*," Appl. Envir. Microbiol., 70(10):6173-6180, 2004.

von Bodman et al., "Capsular polysaccharide biosynthesis and pathogenicity in *Erwinia stewartii* require induction by an N-acylhomoserine lactone autoinducer," J. Bacteriol., 177(17):5000-5008, 1995.

(Continued)

*Primary Examiner*—Medina A. Ibrahim
(74) *Attorney, Agent, or Firm*—Rothwell, Figg, Ernst & Manbeck pc

(57) ABSTRACT

Transgenic plants having resistance against bacterial soft rot diseases, harboring the bacterial autoinducer inactivation gene encoding (AiiA) protein, and methods for protecting plants from bacterial pathogens by transforming the plants with the aiiA gene are disclosed.

14 Claims, 5 Drawing Sheets

OTHER PUBLICATIONS von Bodman et al., A negative regulator mediates quorum-sensing control of exopolysaccharide production in *Pantoea stewartii* subsp. *stewartii*. Proc. Natl. Acad. Sci. USA, 95:7687-7692, 1998.

Whiteley et al., "Regulation of quorum sensing by RpoS in *Pseudomonas aeruginosa*," J. Bacteriol., 182(15):4356-4360, 2000.

Zhang et al., "Pathogenic Signal Manipulation for Disease Resistance," Plant Animal Genome VIII Conference, San Diego, Jan. 9-12, 2000. (Abstract).

* cited by examiner

SEQUENCE LISTING

```
<160> NUMBER OF SEQ ID NOS: 4

<210> SEQ ID NO 1
<211> LENGTH: 78
<212> TYPE: DNA
<213> ORGANISM: Artificial Sequence
<220> FEATURE:
<223> OTHER INFORMATION: Primer-signal peptide coding region of
      Nicotiana plumbaginifolia
```

```
-continued

<400> SEQUENCE: 1
catgtctcga gatggctact caacgaaggg caaaccctag ctctctccat ctaattactg      60
tattctctct gctcgtcg                                                   78

<210> SEQ ID NO 2
<211> LENGTH: 78
<212> TYPE: DNA
<213> ORGANISM: Artificial Sequence
<220> FEATURE:
<223> OTHER INFORMATION: Primer-signal peptide coding region of
      Nicotiana plumbaginifolia

<400> SEQUENCE: 2
tgactaagct tctttactgt catagcggag acgacagcga cgagcagaga gaatacagta     60
attagatgga gagagcta                                                   78

<210> SEQ ID NO 3
<211> LENGTH: 22
<212> TYPE: DNA
<213> ORGANISM: Artificial Sequence
<220> FEATURE:
<223> OTHER INFORMATION: Primer-signal peptide coding region of
      Nicotiana plumbaginifolia

<400> SEQUENCE: 3
catgtctcga gatggctact ca                                              22

<210> SEQ ID NO 4
<211> LENGTH: 22
<212> TYPE: DNA
<213> ORGANISM: Artificial Sequence
<220> FEATURE:
<223> OTHER INFORMATION: Primer-signal peptide coding region of
      Nicotiana plumbaginifolia

<400> SEQUENCE: 4
tgactaagct tctttactgt ca                                              22
```

CONTROL OF BACTERIAL INFECTION BY QUENCHING QUORUM-SENSING OF PLANT PATHOGENIC BACTERIA

BACKGROUND OF THE INVENTION

1. Technical Field

This invention pertains to the field of genetic manipulations of plants, and in particular to introduction of the aiiA gene into plants to quench pathogen quorum-sensing signaling. The invention also relates to transgenic plants expressing the aiiA gene with superior resistance to bacterial pathogens.

2. Description of the Background Art

Plant cells are held together by an intercellular substance (middle lamella) that is composed mainly of pectic compounds. Pathogenic bacterial cells enter plant tissues via wounds or stomata and are confined to the intercellular spaces of plant tissues in the early stage of infection. As infection progresses, pectolytic enzymes produced by the pathogen break down the connective tissue between cells and in cell walls, resulting in maceration symptoms in plants (also known as soft rot). See Collmer and Keen, 1986.

Bacterial plant pathogens produce an array of enzymes which attack host cell components, and these enzymes play important roles in suppression of host defense response and establishment of infection. In bacterial plant pathogens such as *Erwinia carotovora*, the OHHL quorum-sensing signal regulates the production of pectolytic enzymes, cellulase and proteases. See Pirhonen et al., 1993. Pectic polymers are structural constituents of plant primary cell walls and middle lamellae, providing physical support for turgid plant protoplasts, a barrier to bacterial penetration, and a source of host defense-eliciting oligalacturonates. See Collmer and Keen, 1986. Degradation of pectic polymers by the pectolytic enzymes has diverse effects on host-pathogen interactions.

Bacterial pathogens such as *Erw. carotovora* produce virulence factors, such as degradative enzymes, which assist the bacteria in entering plant cells and degrading plant tissues. The production of these factors is controlled by an elegant, density-dependent cell-cell communication mechanism known as quorum sensing. See Pirhonen et al., 1993. Several groups of signal molecules are involved in different microbial quorum sensing systems. See Fuqua et al., 1996; Robson et al., 1997. Among them, the best characterized are the N-acyl homoserine lactones (AHLs), also known as autoinducers (AIs). AHLs are members of a family of widely conserved signal molecules used in the quorum sensing systems of many Gram-negative bacteria. They also are involved in regulation of a diverse range of biological activities including expression of virulence genes of bacterial pathogens such as *Erwinia carotovora, Erw. chrysanthemi, Erw. stewartii, Pseudomonas aeruginosa*, and *Xenorhabdus nematophilus*. See Jones et al., 1993; Passador et al., 1993; Pirhonen et al., 1993; von Bodman and Farrand, 1995; Fuqua et al., 1996; Costa and Loper, 1997; Dunphy et al., 1997. AHLs act as ligands to a Lux-R family transcription factor. The LuxR-AHL-like complex controls the transcription of virulence genes. See Fuqua et al., 1996. AHL can couple to either a positive or a negative transcription factor for gene regulation. The list of pathogens using this signaling mechanism can be further expanded since there are many additional bacterial species that are known to produce AHLs. See Bassler et al., 1997; Cha et al., 1998; Dumenyo et al., 1998.

In the human pathogen *P. aeroguinoisa*, at least two different AI-signaling molecules, N-β-oxododecanoyl-L-homoserine lactone (ODHL) and N-butanoyl-L-homoserine lactone (BHL), and two transcriptional activators, LasR and RhlR/VsmR, influence the expression of a large number of virulence factors, including alkaline protease, elastase, exotoxin A, haemolysin and neuramimidase. See Pearson et al., 1994; Robson et al., 1997. The LasR-ODHL complex activates expression of both RhlR and the stationary-phase sigma factor RpoS in a regulatory cascade. See Latifi et al., 1995; Latifi et al., 1996; Pesci and Iglewski, 1997; McKnight et al., 2000; Whitely et al., 2000.

In plant pathogen *P. stewartii*, however, the negative transcription factor, EsaR, in conjunction with AHL, regulates virulence factor production. EsaR binds to its target promoters and inhibits transcription in the absence of N-β-oxohexanoyl-L-homoserine lactone (OHHL). Binding of OHHL to EsaR releases its binding from the target promoter and thereby initiates the expression of the virulence factor. See von Bodman et al., 1998. In some other bacteria, such as *Erw. carotovora*, is not clear yet how AHL is involved in regulation of virulence factor production.

Although the target genes regulated by AHLs are extremely varied and regulatory mechanisms are likely diverse, the general mechanism of AHL-mediated quorum sensing signaling is very much conserved. The conserved feature of quorum sensing is that each individual cell produces a low level of quorum sensing molecules which are transported out of the cell. As the cell density increases and the accumulated signal reaches a threshold concentration (due to a high enough bacterial cell density) the AHLs are internalized and bind to their cognate LuxR-like transcription factors in the bacterial cells. This, in turn, activates the expression of virulence factor. Expression of virulence genes, therefore, is activated only when sufficient AHL signal molecules have accumulated. See Fuqua et al., 1996; Robson et al., 1997.

A newly discovered gene encoding a protein which inactivates AHL (aiiA) has been cloned from the Gram-positive bacterium *Bacillus* sp. strain 240B1. Expression of aiiA in *Erw. carotovora* strain SCG1, a pathogen which causes soft rot disease in many plants, significantly reduces the release of OHHL from the pathogen, decreases the extracellular pectolytic enzyme activities, and attenuates pathogenicity in potato, eggplant, Chinese cabbage, carrot, celery, cauliflower, and tobacco (Dong et al., 2000). This confirms the important role of AHL in regulation of virulence genes.

SUMMARY OF THE INVENTION

Accordingly, the present invention provides a method of quenching quorum sensing of plant pathogenic bacteria in a plant comprising transforming the plant with the aiiA gene or a functional fragment or modification thereof. In another embodiment, the invention provides a method of protecting plants from bacterial pathogens, comprising transforming the plants with the aiiA gene or a functional fragment or modification thereof. In yet a further embodiment, the invention provides plants protected by the method described above and transgenic plants and plant cells which express AiiA.

CaMV35S indicates cauliflower mosaic virus 35S promoter; nos3 indicates nopaline synthase transcription terminator.

Figure 2A:
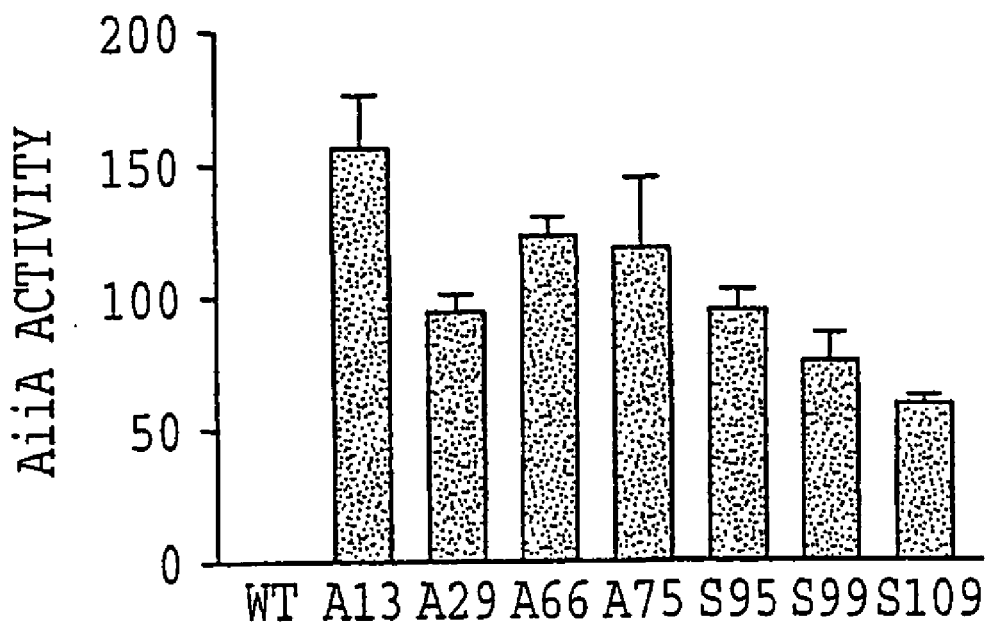
Figure 2B:
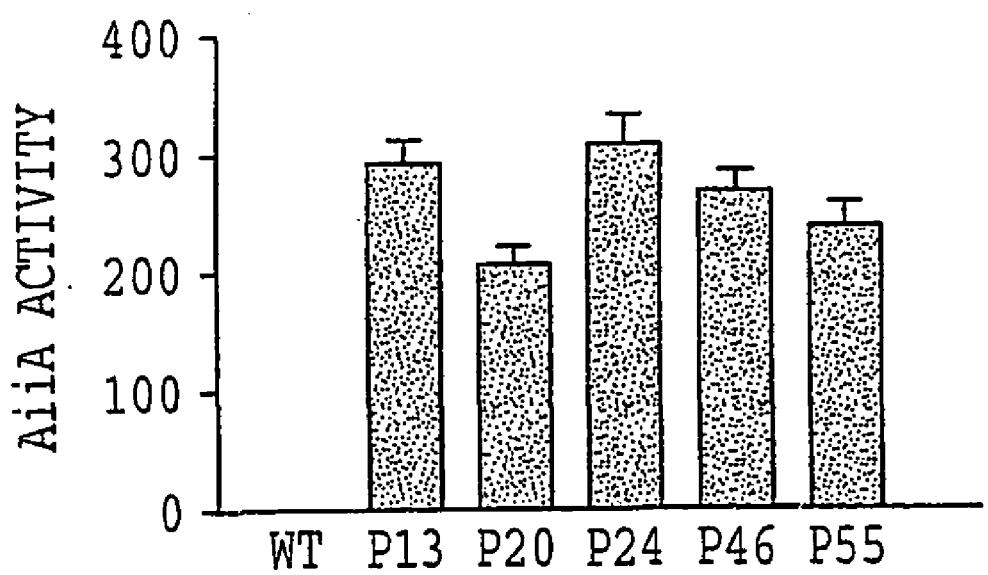

FIG. 2 presents AiiA enzyme activity (nmoles/h/µg protein) in several transgenic tobacco (2A) and potato (2B) cell lines versus wild type (WT).

Figure 3A:
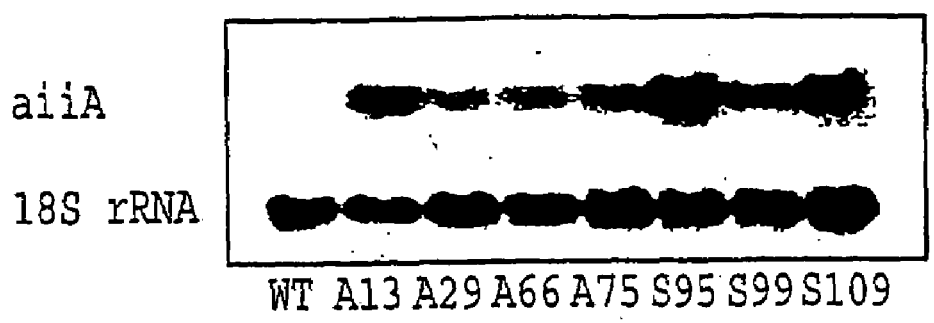
Figure 3B:
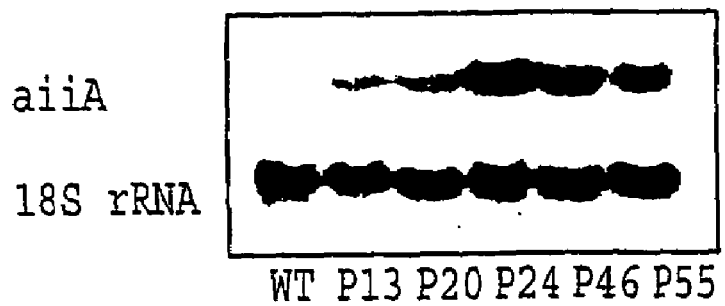

FIG. 3 shows RNA hybridization results for the transgenic tobacco (3A) and potato (3B) cell lines shown in FIG. 2 versus wild type (WT).

Figure 4:
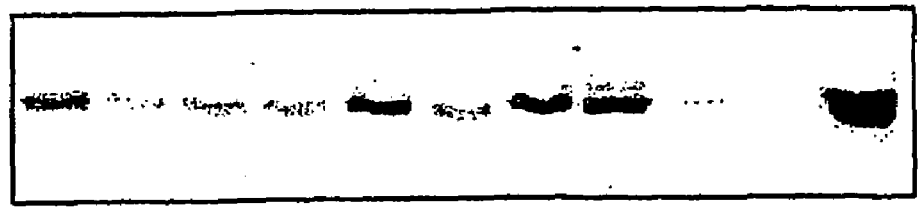

FIG. 4 gives AiiA protein immunoblot data for the indicated transgenic cell lines probed with a polyclonal rabbit anti-AiiA antiserum.

FIG. 5 presents maceration area ($mm^2$) data for transgenic tobacco (5A) and potato (5B) plant tissue from the indicated lines after inoculation with *Erw. carotovora*.

Figure 6A:
Figure 6B:
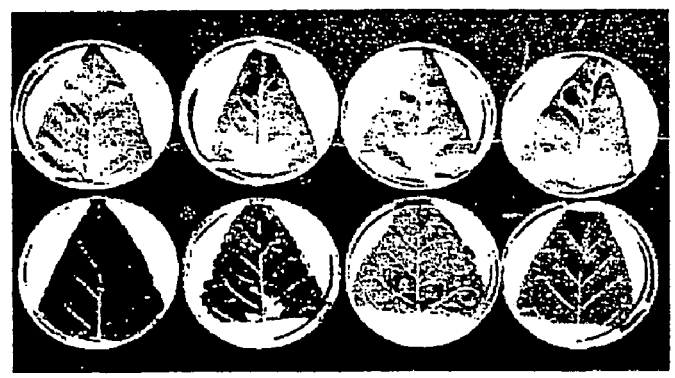
Figure 6C:
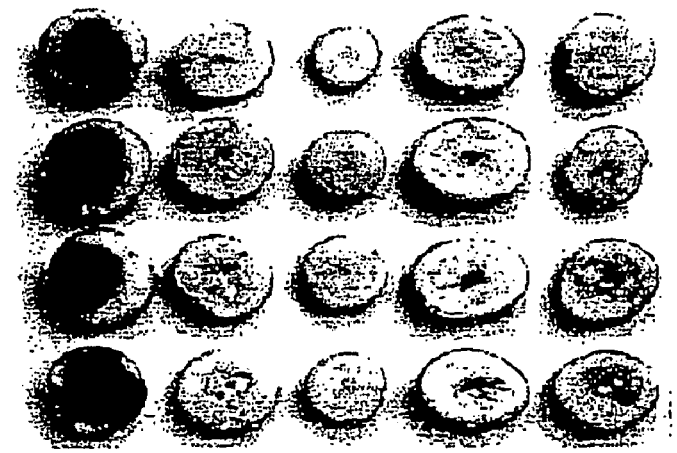

FIG. 6 shows plant tissues challenged with *Erw. carotovora*. FIGS. 6A and 6B depict, from left to right, lines A13, A29, A66 and A75 (top row) and W6, W7, W9 and G7 (bottom row). The tuber slices in columns of FIG. 6C from left to right are from wild type, and potato aiiA transformed lines P46, P24, P55, and P13 respectively.

DETAILED DESCRIPTION OF THE PREFERRED EMBODIMENTS

In the present invention, a gene (aiiA) which encodes an AHL inactivation enzyme (AiiA) was introduced into the plant genome to produce genetically modified plants capable of quenching pathogen quorum-sensing signaling. The trangenic plants expressing the AiiA enzyme showed a significantly enhanced resistance to infection by bacterial pathogens and delayed development of soft rot symptoms even when a high cell density bacterial inoculum (about 60,000 bacterial cells per inoculation site) was applied to wounded plant tissue. The results demonstrate the feasibility of using quorum-sensing signals as targets for disease control, thereby broadening the potential approaches for prevention of bacterial infections.

The methods and plants of this invention, therefore represent a new and effective method of protecting crop and ornamental plants such as potato, eggplant, Chinese cabbage, carrot, celery, cauliflower, tobacco, maize, agave, cotton, rice, grapevine, sugarbeet, hyacinth, iris, cyclamen, onion, radish, squash, tomato, and any other plants susceptible to bacterial soft rot disease. This approach can be used with any plant which is susceptible to bacterial pathogen attack. Plants harboring the aiiA gene are protected from any bacterial pathogen which uses AHL quorum sensing signals, including *Erw. carotovora* pv. *carotovora*, *Erw. carotovora* pv. *atroseptica*, *Erw. carotovora* subsp. *betavasculorum*, *Erw. chrysanthemi*, *Erw. stewartii* pv. *stewartii* and any other pathogens in which expression of virulence genes is controlled by acyl homoserine lactone quorum sensing signals.

To produce transgenic plants protected from bacterial disease, two different aiiA constructs, one lacking a secretion signal peptide and one fused to a plant secretion signal peptide were created. The plants transformed with the gene lacking a signal peptide were designed to constitutively produce cytoplasmic AiiA enzyme, whereas those containing the fused 27 amino acid calreticulin signal peptide (Borisjuk et al., 1999) were designed to secrete the enzyme. The signal peptide (SP) of tobacco calreticulin protein has been used for targeting the GFP protein to the secretory pathway and intercellular spaces of tobacco. See Borisjuk et al., 1999.

Methods of genetic manipulation and transformation of plant cells are well known in the art, as are methods of regenerating fertile, viable transformed plants. In general, any method of cloning the coding region or a functional fragment or modification thereof into a suitable expression vector may be used. It is into a suitable expression vector may be used. It is convenient to ligate the aiiA coding region into vector pBluescript Sk from pGEM7-aiiA, as described in Example 1, followed by ligation into a plant transformation vector, however those of skill are well aware of alternative methods to achieve the same results.

Any suitable plant transformation vector may be used. The vector must contain the aiiA gene, or a functional fragment or modification thereof, so long as expression of the gene results in the production of an AiiA protein or functional fragment or modification thereof which is able to inactivate AHL. By "functional fragment or modification thereof," it is meant any fragment, variant or mutation which encodes a protein sequence capable of inactivating n-acyl homoserine lactones.

A functional promoter, for example CaMV, 355 preferably controls expression. The maximum aiiA translational expression level under the control of the CaMV 35S promoter corresponded to 0.0007% and 0.011% of water soluble proteins respectively in tobacco leaves and in potato tubers. It is possible to optimize the aiiA expression by modification of codon usage (Perlak et al., 1991) and coupling to a strong promoter such as the double 35S promoter (Sharma et al., 1998).

A suitable marker gene, such as kanamycin resistance, green fluorescent protein or any other convenient marker is advantageously used. Variations of the exemplary methods provided in Example 1, which describes one method of transforming plants with the aiiA gene, are well within the skill of the ordinary artisan in genetic manipulation of plants. Expression secretion of the expressed AiiA protein, or may lack such a sequence, as desired. The plant transformation vectors containing the aiiA gene and a kanamycin resistance marker gene were used in Example 1 to transform both tobacco and potato plant cells using *Agrobacterium*-mediated transformation. *Agrobacterium*-mediated transformation is conveniently used to transform plants with the aiiA gene, however any suitable method known in the art may be used, depending on the plant being transformed. For example, certain monocotyledonous plants are more efficiently transformed using other methods such as microprojectile bombardment, vacuum filtration or any other method known in the art to introduce and integrate DNA plasmids or fragments into the plant genome. Those of skill in the art are familiar with means to transform gymnosperms, monocots and dicots. All of these methods known in the art are contemplated for use with this invention.

After selection for transformants carrying the aiiA gene, transgenic tobacco and potato plants may be regenerated. Tobacco and potato plants selected for a marking gene, for example kanamycin resistance, may be assayed, for example by PCR and DNA gel blot to determine how many copies of the aiiA gene are present in the plant. AiiA enzyme activity was detected in transgenic plants transformed with the aiiA gene. The plants were able to inactivate the quorum-sensing signal molecule OHHL, whereas untransformed or GFP control transformed plants were not. There was no correlation between enzyme activity and gene copy number, however AiiA activity was generally lower in number, however AiiA activity was generally lower in plants transformed with the signal peptide-aiiA fusion gene compared to plants transformed with the aiiA gene alone. See FIG. 2 for AiiA enzyme activity data from seven tobacco and five potato plant lines.

Transcription of the aiiA transgene was determined by RNA hybridization, and showed the presence of RNA transcripts in all lines tested with varied levels. See Example 3 for methods. No aiiA transcript or homolog was detected in the untransformed control plants. See FIG. 3. Among the 12 transgenic lines tested, the tobacco lines A13, S95 and S109 and the potato lines p24 and P46 showed the greatest levels of the aiiA transcriptional expression.

Western immunoblots of soluble proteins extracted from tobacco leaves and potato tubers probed with rabbit polyclonal anti-AiiA antibodies detected the AiiA protein as well. As shown in FIG. 4, AiiA was constitutively expressed in these plants, but was undetectable in the untransformed control plants. The lines with higher AiiA enzyme activities, such as A13, P13, P24, and P46, also showed stronger immunoblot signals. Compare FIGS. 2 and 4.

Challenge of wounded plant tissue showed that presence of the transgene conveyed a high level of protection from bacterial pathogens such as *Erw. carotovora*. See FIGS. 5 and 6. The enhanced resistance level of the aiiA transgenic plants is consistent with the ability of the AiiA enzyme to inactivate the OHHL quorum-sensing signal of *E. carotovora* (FIG. 2). The transgenic plant lines with higher levels of AiiA protein content as determined by western analysis, such as tobacco line A13 and potato line P13, P46 and P24, displayed significantly enhanced resistance to *E. carotovora* infection, indicating a strong correlation between disease resistance and the AiiA enzyme expression level.

Upon challenge with different concentrations of *Erw. carotovora* pathogen, tissue inoculated with higher pathogen density suffered a larger maceration area. See FIG. 6. Each tested tobacco leaf was challenged with three different concentrations of *Erw. carotovora* cells. The control plants, including the untransformed and GFP transgenic tobacco, displayed typical maceration several hours after inoculation at all levels of pathogen concentration. The higher the cell density of the inoculum, the bigger the maceration area on the tobacco leaves (FIG. 6A). In the four aiiA transgenic plants, however, plants inoculated with the low cell density of inoculum (600 c.f.u.) did not develop symptoms of soft rot 20 hours after inoculation. The maceration symptom appeared at spots inoculated with a high cell density of pathogen (60,000 c.f.u.), but the macerated areas were much smaller than that of the controls. See FIG. 6A. Similar results were obtained from the control and transgenic potato lines when challenged with pathogen inocula of different cell densities (25,000 B 100,000 c.f.u.). See FIG. 6C.

The results disclosed here demonstrate that expression of the AiiA enzyme dramatically retards the development of bacterial disease symptoms and permits plants to fight bacterial infection and recover quickly. Forty hours after inoculation, all tested leaves of wild type tobacco were macerated, whereas the aiiA transgenic tobacco leaves showed no significant development of maceration. See FIG. 6B. Similar results were observed in aiiA transgenic potato. Typical soft rot symptoms were observed in the tuber slices of control plants even after two days. The water-soaked lesions of the untransformed control enlarged rapidly in diameter and in depth. In contrast, the high cell density bacterial inoculum caused watery lesions in the aiiA transgenic potato tuber tissues, but the lesions dried and the symptom development was arrested. See FIG. 6C. There is a strong negative correlation between the AiiA content and the area of plant tissue maceration. The lines with high AiiA content show no symptom or significantly less tissue maceration compared to the lines with low AiiA content and the untransformed controls. The expression of the transgene protected plants by slowing down the pathogen's ability to produce virulence factors including pectolytic enzymes, allowing the host defense response to eventually stop the infection. Expression of the AiiA enzyme prevented the bacteria from overwhelming plant defenses.

The trancriptional expression levels of the sp-aiiA fusion gene in the three lines tested are higher than that of the best aiiA trangenic lines (as judged by the signal intensity of northern blot), but the enzyme activities and the resistance levels of these sp-aiiA lines are slightly poorer than those of the best aiiA lines. One possibility for this is that the secreted enzyme is trapped in the microsomes as in the case of calreticulin protein (Borisjuk et al., 1998) slowing down the speed of contact between the AiiA enzyme and the OHHL quorum-sensing signal.

The results presented here show that the aiiA gene/enzyme can confer a broad spectrum of resistance to microbial infections. A diverse range of acyl homoserine lactone (AHL) derivatives have been identified from Gram-negative bacteria. AiiA enzyme effectively inactivated all the AHL members tested, including N-(3-oxohexanoyl)-homoserine lactone from *Erw. carotovora*, N-(3-oxododecanoyl)-homoserine lactone from *Pseudomonas aeruginosa*, and N-hydroxybutyryl-homoserine lactone from *Vibrio harveyi*. See Dong et al., 2000. Therefore, the methods of protecting plants and quenching quorum sensing of pathogenic bacteria may be used to protect any susceptible plant from any bacteria which uses quorum sensing with acyl homoserine lactones. In addition to the transgenic approach, bacterial strains containing the aiiA gene also could be developed as biocontrol agents, and the AiiA enzyme could be used for coating medical utensils.

The following examples are provided to illustrate the invention and are not intended to be limiting.

EXAMPLE 1

Transformation of Plants with the aiiA Gene

Figure 1:
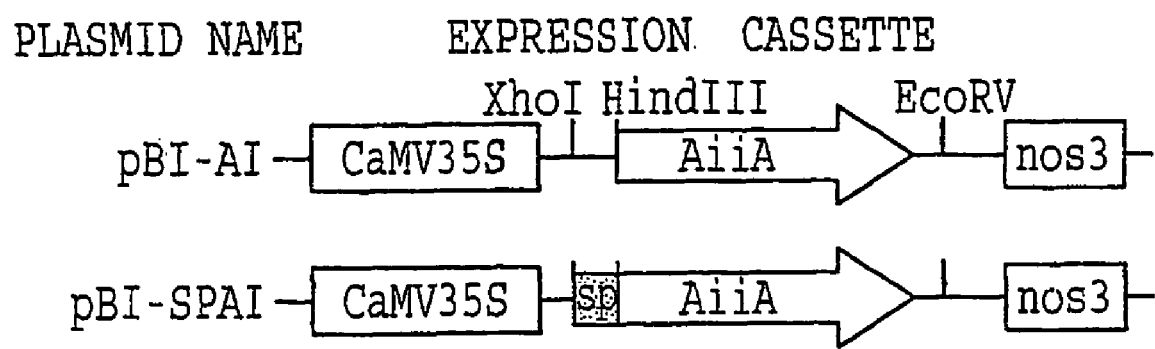
FIG. 1 shows a diagram of the expression cassettes used to transform plant cells. The cassettes express the aiiA gene (pBI-AI) and the sp-aiiA fusion gene (pBI-SPAI). sp indicates the signal peptide from tobacco calreticulin.

Two aiiA gene constructs were generated for transformation of tobacco and potato. The DNA fragment containing the aiiA coding region was produced by digestion of pGEM7-aiiA (Dong et al., 2000; accession number AF196486) with KpnI and EcoRV. The fragment was ligated into the cloning vector pBluescript SK to produce pBS-aiiA. A XhoI-SacI fragment containing the aiiA from pBS-aiiA was ligated into the plant transformation vector pBI121 between the CaMV 35S promoter and the *Agrobacterium nos* terminator to generate the construct pBI-AI which contains a kanamycin resistance gene as the selection marker. See FIG. 1.

For generation of a fusion gene encoding for a signal peptide-AiiA fusion protein which could be targeted into plant intercellular spaces, the signal peptide (SP) coding region of *Nicotiana plumbaginifolia* calreticulin protein (Borisjuk et al., 1998; accession number Z71395) was generated by PCR amplification. The primers were: Spf, 5'-CAT GTC TCG AGA TGG CTA CTC AAC GAA GGG CAA ACC CTA GCT CTC TCC ATC TAA TTA CTG TAT TCT CTC TGC TCG TCG-3' (SEQ ID NO:1); Spr, 5'-TGA CTA AGC TTC TTT ACT GTC ATA GCG GAG ACG ACA GCG ACG AGC AGA GAG AAT ACA GTA ATT AGA TGG AGA GAG CTA-3' (SEQ ID NO:2); Spf22, 5'-CAT GTC TCG AGA TGG CTA CTC A-3' (SEQ ID NO:3) and Spr22, 5'-TGA CTA AGC TTC TTT ACT GTC A-3' (SEQ ID NO:4). The resulting PCR fragment contained a sequence encoding for a 27-aa signal peptide and for 6 amino acids at the N-terminus of the AiiA protein, as well as sequences for restriction sites to facilitate cloning (shown in italics). After digestion with XhoI and HindIII, the PCR product was cloned into the XhoI/HindIII sites of pBS-aiiA to generate the sp-aiiA fusion gene in plasmid pBS-SPAI shown in FIG. 1. The XhoI-SacI fragment containing the sp-aiiA fusion gene from the pBS-SPAI was cloned into pBI121 to generate the pBI-SPAI. AiiA secretion by cells transformed with the second construct was confirmed by transfection of E. coli DH5α with each of the two constructs. AiiA activity was detected in the supernatant of E. coli DH5α transfected with pBS-SPAI but not in that of E. coli DH5α transfected with pBS-AI, indicating that the signal peptide directed the secretion of AiiA protein. The coding region of the green fluorescence protein (GFP) was cloned in pBI121 to produce the control construct pBI-GFP.

Tobacco (Nicotiana tabacum L., cv. GX3) and potato (Solanum tuberosum L. cv. Bintje) plants were transformed using an Agrobacterium coculture method as discussed in Gallois and Marinho, 1995 and Beaujean et al., 1998. The pBI-AI, pBI-SPAI and pBI-GFP constructs respectively were introduced into the A. tumefaciens strain LBA 4404 by the freeze-thaw method as described by Walkerpeach and Velten, 1994.

Tobacco leaf discs and potato tuber and young internode explants were used for transformation. The tuber slices were taken from mature tubers, and the leaf discs and young internodes (~5 mm) were from 4–5 week old plants. The explants were submerged in a fresh Agrobacterium suspension (O.D.$_{600}$=0.4) for 30 min and then co-cultured at 25° C. for two days in callus induction medium (CIM). For tobacco, CIM included MS basal salt mixture (Sigma M5524) supplemented with 30 g/L sucrose, 0.1 mg/L NAA and 1 mg/L 6-BA. For potato CIM, 30 g/L sucrose, 2 mg/L zeatin riboside and 1 mg/l IAA were added to the MS basal salt mixture. After co-culture, explants were transferred to selection medium (SM), which included all the components of CIM plus kanamycin (120 mg/l) and cefataxime (100 mg/l) for tobacco. Selection medium used for transgenic potato selection was prepared in the same way except the plant hormones were optimized by replacing the IAA with 2 mg/L GA3 and reducing the amount of zeatin riboside to 0.8 mg/L. Transgenic plants on SM were grown under standard conditions (25° C., 16L/8D) in growth chambers.

A total of 155 independent kanamycin resistant tobacco plants were generated, 60 from tissues harboring pBI-AI and 95 from tissues harboring pBI-SPAI. Five untransformed plants and 5 plants transformed with the pBI green fluorescent protein (GFP) construct also were regenerated to serve as is controls. PCR tests from 57 randomly selected kanamycin resistant plant lines indicated that 91.2% were positive for the aiiA gene. For potato, a total of 50 plants were generated, 36 from cells harboring pBI-AI and 14 from cells harboring pBI-SPAI. Three untransformed and 2 pBI-GFP transformed potato plants were produced to serve as controls. DNA gel blot analysis of 10 tobacco lines and 11 potato lines showed that the transgenic plants had 1–4 copies of the aiiA gene. Neither obvious differences in growth and development, nor significant phenotypic changes were observed in these plants compared to parental, untransformed plants.

EXAMPLE 2

Protein Extraction and Assay for AiiA Enzyme

To test for AiiA enzyme activity in the transgenic plants, total soluble protein was extracted from tobacco leaves and potato tubers by homogenizing 1 g fresh tobacco leaf tissue with 1.5 ml protein extraction buffer (100 mM Tris-HCl, pH 8.0; 10 mM MgCl$_2$; 18% (w/v) sucrose; 40 mM 2-mercaptoethanol) or 1 g potato tuber tissue with 1.0 ml protein extraction buffer. The homogenates were sedimented at 10,000×g for 15 min at 4° C. to remove debris. The supernatant was then used for both protein and enzyme activity assay. Protein concentration was determined by the Bio-Rad™ protein assay method according to manufacturer's instructions, using bovine serum albumin as a standard.

AiiA enzyme activity was assayed by adding different amounts of the total protein extracts (5, 10 or 20 μl) to 10 μl of 40 μM OHHL in a total volume of 30 μl and incubating the mixture for 30 min at 28° C. The digested OHHL concentration was determined by plate assay, as previously described by Dong et al., 2000. AiiA activity was defined as nmoles OHHL digested per hour per μg of total protein (nmoles/h/μg protein).

Most of the transgenic plants tested inactivated OHHL, but no AiiA enzyme activity was detected in untransformed plants or GFP control transgenic plants. Different levels of AiiA activity were observed among the transgenic plants, however there was no correlation detected between enzyme activity and aiiA gene copy number. FIG. 2 shows AiiA enzyme activity from seven tobacco and five potato cell lines. Enzyme activities ranged from 70 to 300 nmoles/h/μg protein. The AiiA activity in the plants transformed with the signal peptide-aiiA fusion gene (sp-AiiA) was generally lower than that in those transformed with the aiiA gene only. See FIG. 2. In this figure and in FIGS. 3 and 4, plant cell lines beginning with "A" indicate tobacco aiiA transformants. "S" indicates tobacco sp-aiiA transformants and "P" indicates potato aiiA transformant cell lines.

EXAMPLE 3

Expression Analysis of Transgenic Plants

Transcription expression of the aiiA gene in transgenic tobacco and potato was determined by RNA hybridization. Total RNA was extracted from tobacco and potato leaves by the TRIZOL method (Gibco-BRL). Total RNA (10 μg) was fractionated in 1.2% formaldehyde-agrose gels and transferred to Hybond —N$^+$ (Amersham) nylon membranes. The aiiA coding region and the tobacco 18S rRNA fragment was radiolabelled with α-p$^{32}$-dCTP using the random prime labeling system (Rediprime™ II, Amersham). The RNA samples were hybridized initially with the aiiA probe and then with the 18S rRNA probe to confirm equivalent RNA loading. After hybridization, the membranes were washed twice for 30 min in 2×SSC (17.53 g/L NaCl, 8.82 g/L sodium citrate, pH 7.0) containing 0.1% SDS at 65° C. and twice for 30 min in 0.2×SSC containing 0.1% SDS at 65° C. See FIG. 3, which provides the RNA gel blot data. All tested lines contained RNA transcripts, confirming transcription of the aiiA transgene. Wild type (WT) plants did not contain detectable aiiA RNA.

AiiA protein was purified by selective binding of the GST-AiiA fusion protein from cell extracts of transformed E. coli cells to glutathione affinity resins and subsequent releasing the AiiA from the bound fusion protein by a site-specific protease. Purified AiiA was used to raise anti-AiiA antiserum in rabbits.

Immunoblot analysis was used for detection of AiiA protein in transgenic plants. See FIG. 4. "WT" indicates wild type (untransformed) control. The "AiiA" lane contains 10 ng purified AiiA protein. Protein samples normalized for protein content were separated by 12% SDS-PAGE and transferred onto PVDF membranes (Bio-Rad). The blots then were probed with polyclonal rabbit anti-AiiA antibodies, followed by alkaline phosphatase-conjugated secondary antibodies. Signals were quantified by scanning the blotted membrane with an Imaging Densitometer (Bio-Rad). Using purified AiiA in serial dilution as standards for immunoblot analysis, the AiiA protein content was estimated to be from 2–7 ng/mg soluble protein in tobacco leaves and 20–110 ng/mg soluble protein in potato tubers. As expected, the SP-AiiA fusion proteins from tobacco lines S95, S99 and S109 were detected in both the water-soluble and microsomal fractions (data not shown).

EXAMPLE 4

Challenge to Disease by Bacterial Pathogen *Erw. carotovora* SCG1

Transgenic tobacco and potato plants were assayed for resistance to the pathogen *Erw. carotovora*. Thirty-eight transgenic lines of tobacco plants (20 of the aiiA lines and 18 of the sp-aiiA lines) and 35 lines of potato plants (29 of the aiiA lines and 6 of the sp-aiiA lines) were randomly selected for inoculation assay. An overnight culture of *Erw. carotovora* SCG1 bacteria was sedimented, resuspended and adjusted to different cell densities in phosphate buffer (pH 8.0). For assay of tobacco, leaves of similar size excised from 5–8 week old tobacco plants were wounded (punched slightly with a 20-μl pipette tip) and placed on a plastic plate that contained one layer of Whatman filter paper wetted with 2 ml of sterile water. The leaves were inoculated by adding 3 μL of *Erwinia* SCG1 at a concentration of $2 \times 10^7$, $2 \times 10^6$ or $2 \times 10^5$ colony forming units (c.f.u.) per ml on the wounded surface of the leaves. For potato assay, tubers were rinsed in tap water and surface-sterilized with 70% ethanol. The tubers were cut evenly into 3-mm slices. The potato slices were placed on the plastic plates in the same way as the tobacco leaves. The slices were lightly punched with a pipette tip and inoculated with 5 μl of *Erwinia* SCG1 suspension ($2 \times 10^7$ c.f.u. per ml). The plastic plates containing the inoculated plant tissues were incubated at 28° C. for 20 hours (tobacco) or 48 hours (potato) before measurement of maceration areas. When challenged with an inoculum corresponding to 6000 c.f.u. (tobacco) or 100,000 c.f.u. (potato), control plants (untransformed and GFP transgenic) showed typical soft rot symptoms, whereas 89.5% of transgenic tobacco lines and 88.6% of transgenic potato lines showed elimination or reduction of tissue soft rot.

Figure 5A:
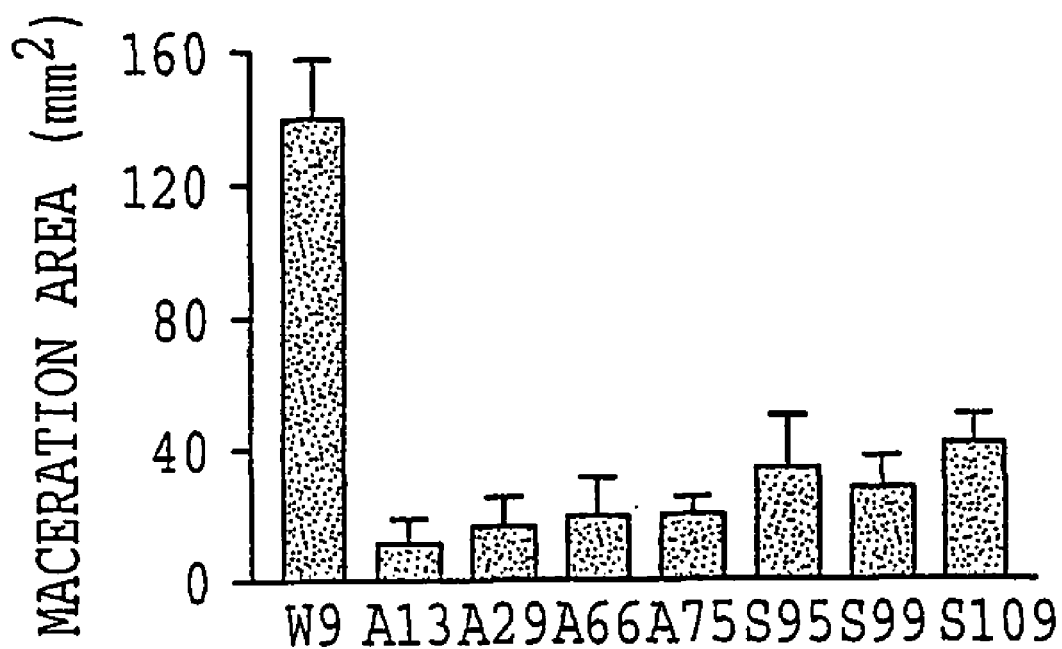
Figure 5B:
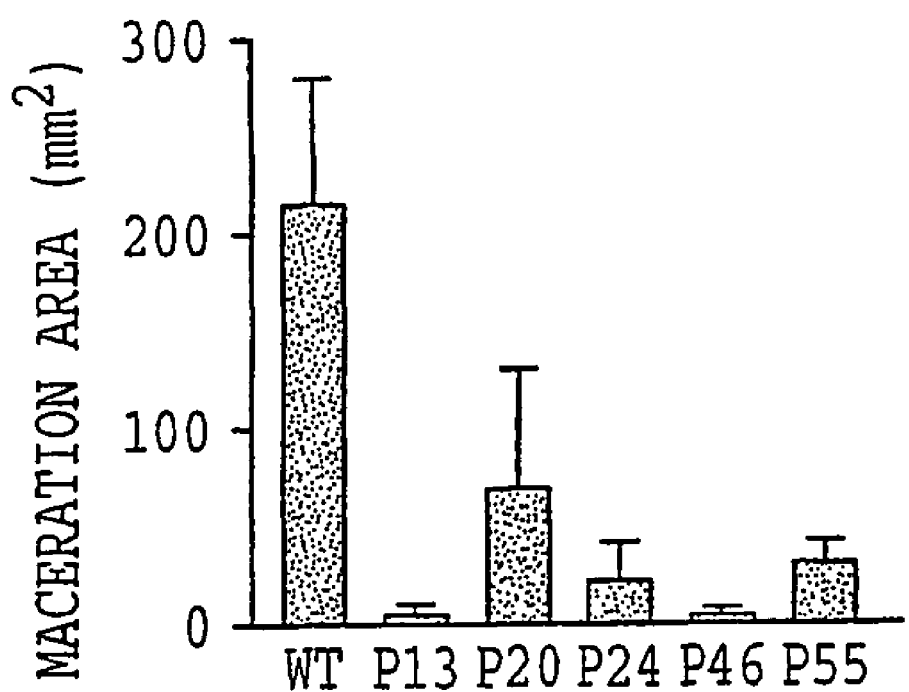

FIGS. 5A and 5B show the average areas of maceration of control plants and the tested transgenic tobacco and potato plants. The data shown in FIG. 5 pertains to plants inoculated with *Erw. carotovora* at $2 \times 10^6$ c.f.u. per ml (tobacco) or $2 \times 10^7$ c.f.u. per ml (potato). The data were means of 8 (for tobacco) or 6 (for potato) replicates. Vertical bars represent the standard error. The cell density per inoculation site was $6 \times 10^3$ c.f.u. in a volume of 3 μl for tobacco or $1 \times 10^5$ c.f.u. in a volume of 5 μl for potato. The untransformed plants (WT) were used as controls. FIG. 6 shows tobacco leaves (A, B) and potato tuber slices (C) following inoculation with *Erw. carotovora* SCG1.

Each leaf was inoculated in the same order with 3 SCG1 inocula of varied cell densities on 6 sites, which are indicated by the visible maceration spots on the control leaves. The inocula cell numbers on the two top spots, the two spots on the lower left side, and the two spots on the lower right side of each leaf were 60,000, 6,000, and 600 c.f.u. respectively. The photograph of FIG. 6A was taken 20 hours after inoculation. FIG. 6B is the same as A except the photograph was taken 40 hours after inoculation. FIG. 6C shows potato tuber slices inoculated with SCG1 inocula of 4 cell densities. The inoculated bacterial cell numbers for the rows (from top to bottom) were 25,000, 50,000, 75,000, and 100,000 c.f.u. respectively. The photograph for FIG. 6C was taken 48 hours after inoculation.

REFERENCES

Andersson, R. A., Eriksson, A. R., Heikinheimo, R., Mae, A., Pirhonen, M., Koiv, V., Hyytiainen, H., Tuikkala, A., and Palva, E. T. (2000). Quorum sensing in the plant pathogen *Erwinia carotovora* subsp. *carotovora*: the role of expR(Ecc). *Mol Plant-Microbe Interact* 13:384–93.

Barber, C. E. Tang, J. L., Feng, J. X., Pan, M. Q., Wilson, T. J., Slater, H., Dow, J. M., Williams, P., and Daniels M. J. (1997). A novel regulatory system required for pathogenicity of *Xanthomonas campestris* is mediated by a small diffusible signal molecule. *Mol Microbiol* 24: 555–556.

Bassler, B. L., Greenberg, E. P., and Stevens, A. M. (1997). Cross-species induction of luminescence in the quorum-sensing bacterium *Vibrio harveyi*. *J Bacteriol* 179:4043–4045.

Beaujean, A., Sangwan, R. S., Lecardonnel, A., and Sangwan-Norreel, B. S. (1998). *Agrobacterium*-mediated transformation of three economically important potato cultivars using sliced internodal explants: an efficient protocol of transformation. *J Exp Bot* 49:1589–1595.

Borisjuk, N., Sitailo, L., Adler, K., Malysheva, L., Tewes, A., Borisjuk, L., and Manteuffel, R. (1998). Calreticulin expression in plant cells: developmental regulation, tissue specificity and intracellular distribution. *Planta* 206:504–14.

Borisjuk, N. V., Borisjuk, L. G., Logendra, S., Logendra, S., Petersen, F., Gleba, Y., and Raskin, I. (1999). Production of recombinant proteins in plant root exudates. *Nature Biotechnol* 17:466–469.

Cha, C., Gao, P., Chen, Y. C., Shaw, P. D., and Farrand, S. K. (1998). Production of acyl-homoserine lactone quorum-sensing signals by gram-negative plant-associated bacteria. *Mol Plant-Microbe Interact* 11:1119–1129.

Chun, W., Cui, J., and Poplawsky, A. (1997). Purification, characterization and biological role of a pheromone produced by *Xanthomonas campestris* pv. *campestris*. *Physiol Mol Pl Pathol* 51, 1–14.

Collmer, A., and Keen, N. T. (1986). The role of pectic enzymes in plant pathogenesis. *Ann Rev Phytopathol* 24: 383–409.

Costa, J. M., and Loper, J. E. (1997). EcbI and EcbR: homologs of LuxI and LuxR affecting antibiotic and exoenzyme production by *Erwinia carotovora* subsp. *betavasculorum*. *Can J Microbiol* 43:1164–71.

Dong, Y.-H., Xu, J.-L., Li, X.-C., and Zhang, L.-H. (2000). AiiA, a novel enzyme inactivates acyl homoserine-lactone quorum-sensing signal and attenuates the virulence of *Erwinia carotovora*. *Proc Natl Acad Sci USA* 97: 3526–3531.

Dumenyo, C. K. M., Chun, A. W., and Chatterjee, A. K. (1998). Genetic and physiological evidence for the production of N-acyl homoserine lactones by *Pseudomonas syringae* pv. *syringae* and other fluorescent plant pathogenic *Pseudomonas* species. *Euro J Plant Pathol* 104: 569–582.

Dunphy, G., Miyamoto, C., and Meighen, E. (1997). A homoserine lactone autoinducer regulates virulence of an insect-pathogenic bacterium, *Xenorhabdus nematophilus* (Enterobacteriaceae). *J Bacteriol* 179:5288–5291.

Flavier, A. B., Clough, S. J., Schell, M. A., and Denny, T. P. (1997). Identification of 3-hydroxypalmitic acid methyl ester as a novel autoregulator controling virulence in *Ralstonia solanacearum*. *Mol Microbiol* 26, 251–259.

Fuqua, C., Winans, S. C., and Greenberg, E. P. (1996). Census and consensus in bacterial ecosystems: the LuxR-LuxI family of quorum-sensing transcriptional regulators. *Annu Rev Microbiol* 50:727–751.

Gallois, P., and Marinho, P. (1995). Leaf disc transformation using *Agrobacterium tumefaciens*-expression of heterologous gene in tobacco. In: H. Jones (Ed) Plant gene transfer and expression protocols, Humana press, Totowa, N.J., pp. 39–48.

Ji, G., Beavis, R. C., and Novick, R. P. (1995). Cell density control of staphylococcal virulence mediated by an octapeptide pheromone. *Proc Natl Acad Sci USA* 92: 12055–12059.

Jones, S. M., Yu, B., Bainton, N. J., Birdsall, M., Bycroft, B. W., Chhabra, S. R., Cox, A. J. R., Golby, P., Reeves, P. J., Stephens, S., Winson, M. K., Salmond, G. P. C., Stewart, G. S. A. B., and Williams, P. (1993). The Lux autoinducer regulates the production of exoenzyme virulence determination in *Erwinia carotovora* and *Pseudomonas aeruginosa*. *EMBO J*. 12:2477–2482.

Kaplan, H. B., and Greenberg, E. P. (1985). Diffusion of autoinducer is involved in regulation of the *Vibrio fischeri* luminescence system. *J Bacteriol* 163: 1210–1214.

Latifi, A., Winson, M. K., Foglino, M., Bycroft, B. W., Stewart, G. S., Lazdunski, A., and Williams, P. (1995). Multiple homologues of LuxR and LuxI control expression of virulence determinants and secondary metabolites through quorum sensing in *Pseudomonas aeruginosa* PAO1. *Mol Microbiol* 17:333–43.

Latifi, A., Foglino, M., Tanaka, K., Williams, P., and Lazdunski, A. (1996). A hierarchical quorum-sensing cascade in *Pseudomonas aeruginosa* links the transcriptional activators LasR and RhlR (VsmR) to expression of the stationary-phase sigma factor RpoS. *Mol Microbiol* 21:1137–46.

McKnight, S. L., Iglewski, B. H., and Pesci, E. C. (2000). The *Pseudomonas quinolone* signal regulates rhl quorum sensing in *Pseudomonas aeruginosa*. *J Bacteriol* 182: 2702–8.

Passador, L., Cook, J. M., Gambello, M. J., Rust, L., and Iglewski, B. H. (1993). Expression of *Pseudomonas aeruginosa* virulence genes requires cell-to-cell communication. *Science* 260:1127–1130.

Pearson, J. P., Gray, K. M., Passador, L., Tucker, K. D., Eberhard, A., Iglewski, B. H., and Greenberg, E. P. (1994). Structure of the autoinducer required for expression of *Pseudomonas aeruginosa* virulence genes. *Proc Natl Acad Sci USA* 91:197–201.

Perlak, F. J., Fuchs, R. L., Dean, D. A., McPherson, S. L., and Fischhoff, D. A. (1991). Modification of the coding sequence enhances plant expression of insect control protein genes. *Proc Natl Acad Sci USA* 88:3324–3328.

Pesci, E. C., and Iglewski, B. H. (1997). The chain of command in *Pseudomonas* quorum sensing. *Trends Microbiol* 5:132–4.

Pirhonen, M., Flego, D., Heikinheimo, R., and Palva, E. (1993). A small diffusible signal molecule is responsible for the global control of virulence and exoenzyme production in the plant pathogen *Erwinia carotovora*. *EMBO J*. 12:2467–2476.

Robson, N. D., Cox, A. R., McGowan, S. J., Bycroft, B. W., and Salmond, G. P. (1997). Bacterial N-acyl-homoserine-lactone-dependent signaling and its potential biotechnological applications. *Trends Biotechnol* 15:458–64.

Sharma, S. B., Hancock, K. R., Ealing, P. M., and White D. W. R. (1998). Expression of a sulfur-rich maize seed storage protein, d-zein, in white clover (*Trifolium repens*) to improve forage quality. *Mol. Breeding* 4: 435–448.

von Bodman, S. B., and Farrand, S. K. (1995). Capsular polysaccharide biosynthesis and pathogenicity in *Erwinia stewartii* require induction by an N-acylhomoserine lactone autoinducer. *J Bacteriol* 177:5000–5008.

von Bodman, S. B., Majerczak, D. R., and Coplin, D. L. (1998). A negative regulator mediates quorum-sensing control of exopolysaccharide production in *Pantoea stewartii* subsp. *stewartii*. *Proc Natl Acad Sci USA* 95:7687–92.

Walkerpeach, C. R. and Velten, J. (1994). *Agrobacterium*-mediated gene transfer to plant cells: cointegrate and binary vector system. In: S. B. Gelvin and R. A. Schilperoort (Eds.) Plant Molecular Biology Manual, 2nd ed., Kluwer Academic Publishers, Dordrecht, Netherlands, pp. B1:1–19.

Whiteley, M., Parsek, M. R., and Greenberg, E. P. (2000). Regulation of quorum sensing by RpoS in *Pseudomonas aeruginosa*. *J Bacteriol* 182:4356–60.

The invention claimed is:

1. A method of quenching quorum sensing of a plant pathogenic bacterium in a plant, comprising transforming said plant with the bacterial autoinducer inactivation (aiiA) gene encoding N-acylhomoserine lactonase.

2. The method of claim 1, wherein said plant pathogenic bacterium is a Gram-negative bacterium.

3. The method of claim 1, wherein said plant pathogenic bacterium expresses virulence genes controlled by acyl homoserine lactone quorum sensing signals.

4. The method of claim 1, wherein said plant pathogenic bacterium is selected from the group consisting of *Erwinia carotovora* pv. *carotovora*, *Erw. carotovora* pv. *atroseptica*, *Erw. carotovora* subsp. *betavasculorum*, *Erw. chrysanthemi*, and *Erw. stewartii* pv. *stewartii*.

5. The method of claim 4, wherein said plant pathogenic Gram-negative bacterium is *Erwinia carotovora* pv. *carotovora*.

6. A method of protecting a plant from a bacterial pathogen, comprising transforming said plant with the bacterial autoinducer inactivation (aiiA) gene encoding N-acylhomoserine lactonase.

7. The method of claim 6, wherein said bacterial pathogen is a Gram-negative bacterium.

8. The method of claim 7, wherein said Gram-negative bacterial pathogen is selected from the group consisting of *Erwinia carotovora* pv. *carotovora*, *Erw. carotovora* pv. *atroseptica*, *Erw. carotovora* subsp. *betavasculorum*, *Erw. chrysanthemi*, and *Erw. stewartii* pv. *stewartii*.

9. The method of claim 8, wherein said Gram-negative bacterial pathogen is *Erwinia carotovora*.

10. The method of any one of claim 6, wherein said plant pathogenic bacterium expresses virulence genes controlled by acyl homoserine lactone quorum sensing signals.

11. A transgenic plant produced by the method according to claim 6, said plant protected from a bacterial pathogen.

12. A transgenic plant which expresses the bacterial AiiA protein.

13. A transgenic plant cell which expresses the bacterial AiiA protein.

14. A method of producing a transgenic plant having soft rot disease resistance, comprising transferring to the plant the bacterial autoinducer inactivation (aiiA) gene encoding N-acylhomoserine lactonase.

* * * * *